United States Patent
Karr et al.

(10) Patent No.: US 10,369,362 B2
(45) Date of Patent: Aug. 6, 2019

(54) NEURAL PROSTHETIC WITH TOUCH-LIKE SENSING

(71) Applicant: ALFRED E. MANN FOUNDATION FOR SCIENTIFIC RESEARCH, Santa Clarita, CA (US)

(72) Inventors: Lawrence J. Karr, Santa Monica, CA (US); Joseph H. Schulman, Santa Clarita, CA (US)

(73) Assignee: The Alfred E. Mann Foundation for Scientific Research, Santa Clarita, CA (US)

( * ) Notice: Subject to any disclaimer, the term of this patent is extended or adjusted under 35 U.S.C. 154(b) by 161 days.

(21) Appl. No.: 13/749,468

(22) Filed: Jan. 24, 2013

(65) Prior Publication Data

US 2014/0207252 A1 Jul. 24, 2014

Related U.S. Application Data

(62) Division of application No. 11/165,796, filed on Jun. 24, 2005, now Pat. No. 8,361,165.
(Continued)

(51) Int. Cl.
*A61B 5/00* (2006.01)
*A61N 1/36* (2006.01)
*A61B 5/053* (2006.01)

(52) U.S. Cl.
CPC ............ *A61N 1/3605* (2013.01); *A61B 5/053* (2013.01)

(58) Field of Classification Search
CPC ........ A61N 1/3605; B25J 13/084; G01L 9/10; G01L 9/12; G01L 9/0072–0075; A61B 5/053
(Continued)

(56) References Cited

U.S. PATENT DOCUMENTS 3,872,455 A * 3/1975 Fuller .................. A61B 5/0002
128/903
4,114,606 A * 9/1978 Seylar ................... A61B 5/031
165/DIG. 401
(Continued)

OTHER PUBLICATIONS

Sabelman et al. "Tactile transducers to replace lost touch sensation" 1994.*
(Continued)

*Primary Examiner* — Max F Hindenburg
(74) *Attorney, Agent, or Firm* — Lewis Roca Rothgerber Christie LLP (57) ABSTRACT

An apparatus and method is related to providing sensing functions that are similar to "human touch" when located in a prosthetic device such as a BION microstimulator that is implanted in a patient. The apparatus includes a power circuit, a communication circuit and a sensor circuit. The power circuit provides power to the communication circuit and the sensor circuit. The sensor cooperates with the communication circuit, which communicates to the brain. The sensor uses various techniques to detect changes in the environment for the surrounding tissue using criteria such as reflectivity, impedance, conductivity, return signal spectrum, return signal rate and return signal phase to name a few. For example, the impedance observed by the sensor changes when: the skin tissue is deformed around the sensor, or when the skin is surrounded by water. The sensory information is interpreted by the brain as an analog of touch or feel.

18 Claims, 9 Drawing Sheets

Related U.S. Application Data (60) Provisional application No. 60/583,478, filed on Jun. 28, 2004.

(58) Field of Classification Search
USPC .......................................... 607/49; 128/897
See application file for complete search history.

(56) References Cited

U.S. PATENT DOCUMENTS

| | | | | |
|---|---|---|---|---|
| 5,986,549 | A * | 11/1999 | Teodorescu | A61B 5/6892 324/207.16 |
| 6,388,255 | B1 * | 5/2002 | Di Maio | G01K 7/343 250/338.1 |
| 6,995,670 | B2 * | 2/2006 | Wadlow | G01D 5/24 324/686 |
| 2002/0151816 | A1 * | 10/2002 | Rich et al. | 600/547 |
| 2004/0111039 | A1 * | 6/2004 | Minamiura | A61B 5/0205 600/513 |
| 2004/0152276 | A1 * | 8/2004 | Nishimura | H01Q 23/00 438/365 |
| 2004/0155715 | A1 * | 8/2004 | Nakamura | H03B 5/36 331/158 |
| 2004/0212443 | A1 * | 10/2004 | Godambe | H03L 7/099 331/173 |
| 2005/0105661 | A1 * | 5/2005 | Miller | H03L 7/0992 375/376 |
| 2006/0097796 | A1 * | 5/2006 | Gomez | H03L 7/1072 331/16 |
| 2006/0117859 | A1 * | 6/2006 | Liu | A61B 5/02152 73/753 |
| 2006/0232269 | A1 * | 10/2006 | Sills | G06F 3/046 324/207.17 |
| 2008/0157877 | A1 * | 7/2008 | Feng | H03L 7/099 331/11 |

OTHER PUBLICATIONS

Sabelman et al. "Tactile transducers to replace lost touch sensation" 1994, (previously provided).*

* cited by examiner

NEURAL PROSTHETIC WITH TOUCH-LIKE SENSING

RELATED APPLICATION DATA

The present application is a divisional of patent application Ser. No. 11/165,796 filed on Jun. 24, 2005 and claims the benefit under 35 U.S.C. § 119(e) to provisional patent application No. 60/583,478, filed on Jun. 28, 2004 and entitled "Touch-Like Sensing In Neural Prosthetics."

FIELD OF THE INVENTION

The present disclosure relates generally to prosthetic devices. More particularly, the present disclosure relates to an apparatus and method for providing sensing functions that are similar to "human touch" when located in a prosthetic device such as a BION microstimulator that is implanted in a patient. BION is a registered trademark of the Boston Scientific Neuromodulation Corporation of Valencia, Calif.

BACKGROUND OF THE INVENTION

Bionics is a discipline focusing on the application of advanced technologies to biological systems. Generally speaking, a bionic is a manufactured device or engineered tissue that substitutes for, or augments, the function of a natural limb, organ or other portion of a biological body. Although commonly thought of within the context of science fiction, significant strides have been made in the field of bionics. Research in bionics offers the possibility of restoring function to impaired and damaged biological systems.

One significant application of bionics is in the area of vision. Over 30 million people have been subject to retinal degenerative diseases. Retinal degenerative diseases can generally be broken into two categories: Retinitis Pigmentosa (RP) and Age-related Macular Degeneration (AMD).

Retinitis Pigmentosa (RP) is a general term for a number of diseases that predominately affect the photoreceptor layer cells of the retina. The injured photoreceptor cell layer reduces the retina's ability to sense light. Most cases of RP affect the mid-peripheral vision first, which sometimes progresses to affect the far-periphery and the central areas of vision. This narrowing of the field of vision (aka "tunnel vision") can sometimes result in complete blindness.

Age-Related Macular Degeneration (AMD) refers to a degenerative condition that occurs most frequently in the elderly, where decreased function is observed in specific cellular layers of the retina's macula. The outer retina and inner retina photoreceptor layer are affected such that patients experience a loss of their central vision, which affects their ability to read and perform visually demanding tasks.

Significant research has been conducted in the areas of artificial vision to develop an artificial silicon retina (ASR). An ASR is a micro-electronic circuit (or microchip) that is implantable in the body and arranged to stimulate damaged retinal cells, allowing the patient to send visual signals to the brain. An ASR contains thousands of light sensitive cells that convert the light into a series of electrical pulses that mimic the functions of the cones and rods in the eye. Clinical trials have been conducted for ASR devices, although currently vision quality is relatively poor. Additional research in ASR-type devices continues to progress and the promise of restored vision, even to the blind, may be within our grasp.

Another significant application of bionics is in the area of hearing. Hearing loss may be either congenital (acquired either genetically or in utero) or acquired. Various types of hearing loss include: conductive hearing loss, sensorineural hearing loss, or neural hearing loss.

Conductive hearing loss is caused by a problem in the outer or middle ear, wherein the sound path is blocked impairing the ability of the eardrum and bones from vibrating. Conductive losses are usually mild or moderate in nature and in some cases a conductive hearing loss can be temporary. In most cases of conductive hearing loss, hearing can be either restored through surgery and/or medication, or improved with hearing aids.

Sensorineural hearing loss is caused by a problem in the inner ear or cochlea. A damaged inner ear does not change sound waves into the tiny electrical pulses that the auditory nerves need to send sound information to the brain. Sensorineural hearing losses are usually permanent and cannot typically be repaired through surgical procedures. Conventional hearing aids can usually help in mild to severe hearing loss.

Neural hearing loss is due to a problem in the nerve pathway, wherein the auditory nerve is damaged or missing such that signals cannot be sent to the brain. In very rare cases, hearing loss is caused by the absence of or damage to the auditory nerve, resulting in a neural hearing loss. Conventional hearing aids are of little benefit because to a neural hearing loss since the nerve is unable to pass on information to the brain.

Cochlear implants can be a very effective option for those with severe, profound hearing loss who obtain little or no benefit from conventional acoustic amplification such as hearing aids. However, cochlear implants will not help unless there is some auditory nerve function. A cochlear implant is an electronic device that consists of two main parts: an internal implanted part called the implant and an external part known as the speech processor. Sounds are picked up by a microphone and turned into an electrical signal. This signal goes to the speech processor where it is "coded" (turned into a special pattern of electrical pulses). The coded electrical pulses are sent to the coil and are then transmitted across the intact skin (by radio waves) to the implant. The implant sends a pattern of electrical pulses to the electrodes in the cochlea. The auditory nerve picks up these tiny electrical pulses and sends them to the brain. The brain recognizes these signals as sound.

The examples described above illustrate but a few applications for bionics. While bionics cannot cure many of the ailments that exist, current developments present a number of opportunities for improving quality of life. Exciting new research in the field of bionics continues in such areas as drug delivery systems for chronic disabilities, neuromuscular stimulation devices that enable the activation or enhancement of motion to replace lost or impaired motor control, micro-stimulators to treat chronic disorders of the central nervous system, as well as many others.

DETAILED DESCRIPTION OF THE PREFERRED EMBODIMENT

Throughout the specification and in the claims, the term "connected" means a direct electrical connection between the things that are connected, without any intermediary devices. The term "coupled" means either a direct electrical connection between the things that are connected or an indirect connection through one or more passive or active intermediary devices. The term "circuit" means one or more passive and/or active components that are arranged to cooperate with one another to provide a desired function. The term "signal" means at least one current signal, voltage signal, electromagnetic wave signal, or data signal. The meaning of "a", "an" and "the" include plural references. The meaning of "in" includes "in" and "on".

Briefly stated, the present disclosure is related to an apparatus and method for providing sensing functions that are similar to "human touch" when located in a prosthetic device such as a BION microstimulator that is implanted in a patient. The apparatus includes a power circuit, a communication circuit and a sensor circuit. The power circuit provides power to the communication circuit and the sensor circuit. The sensor cooperates with the communication circuit, which communicates with the brain. The sensor uses various techniques to detect changes in the environment for the surrounding tissue using criteria such as reflectivity, impedance, conductivity, return signal spectrum, return signal rate and return signal phase to name a few. For example, the impedance observed by the sensor changes when: the skin tissue is deformed around the sensor, or when the skin is surrounded by water. The sensory information is interpreted by the brain as an analog of touch or feel.

Although many of the examples found herein are described within the context of a sensory device that can be used to communicate with a main control unit (MCU), applications of the devices are not so limited. In one example, the sensory device is configured to communicate with other sensory devices (e.g., BION microstimulators that are arranged to "talk" to one another). In another example, the sensory device is configured to communicate with other devices such as BION microstimulators that are arranged to stimulate or influence muscular functions, stimulate nerves to influence or control motor function, as well as others. In yet another example, the sensory device is configured to communicate with a data-logging device that is external to the body (e.g., a computer system, a monitoring system, etc). In still another example, the sensory device is configured in communication with a set of electrodes that are implanted in a neural pathway. In a further example, the sensory device is configured to stimulate or influence a communication path to a sensory system (e.g., another neural path), a physiological control system (e.g., muscular contraction), or the brain. Such examples can be accomplished by mechanisms that are internal to the body (e.g., through an electrode, through another implanted BION microstimulator, or through some other device) or external to the body (e.g., to an external master control unit, an external computing device, etc.). Many varieties of circuits can be arranged to provide such functions where sensory information is relayed, processed, data-logged, or otherwise handled and communicated.

The examples described above are only to be construed as example applications for such sensory devices as described below. Many embodiments of the invention can be made without departing from the spirit and scope of the invention and the invention resides in the claims that follow this disclosure.

The overall operating environment for the present invention will be discussed as follows below with reference to FIGS. 1 and 2.

Example Operating Environment

Figure 1:
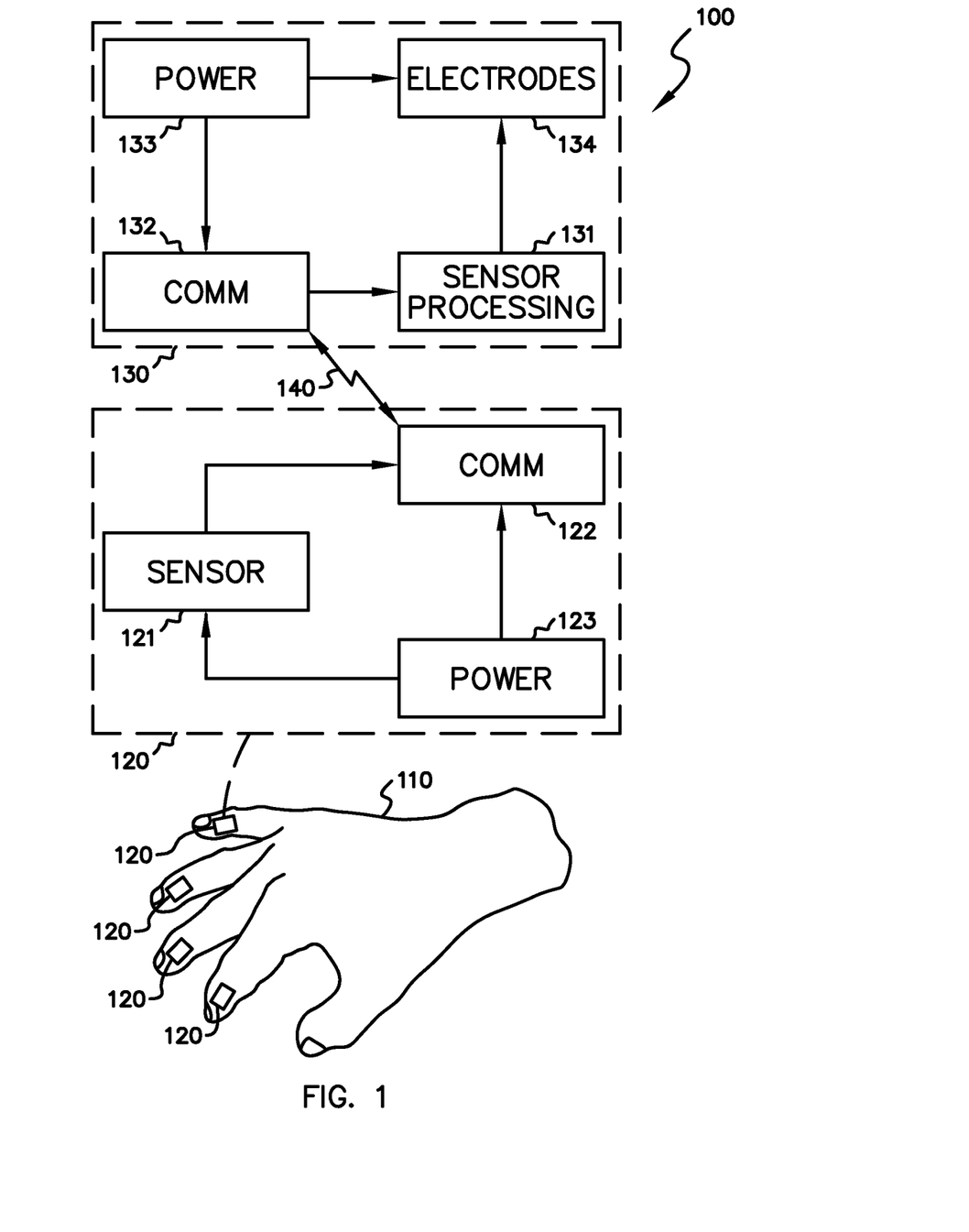
FIG. 1 illustrates an example operating environment for a neural prosthetic device.

FIG. 1 illustrates an example operating environment 100 for a neural prosthetic device. A person may have lost or impaired ability to sense touch in a particular region of the body such as a hand 110. One or more bionic implants 120 are placed in locations where sensor information is desirable. Each of the bionic implants 120 includes sensor circuit 121 and communication circuit 122 that are powered by power source circuit 123. Sensor circuit 121 provides sensory information to communication circuit 122, which subsequently communicates information to the brain. The brain receives the sensory information and interprets the sensory information as touch or feel.

In one example, the communication circuit is arranged to provide a wireless communication signal 140 to master control unit (MCU) 130 that may be implanted in the body (e.g., coupled to a neural pathway), or it may be external to the body. For this example, MCU 130 includes sensor processing circuit 131 and communication circuit 132 that are powered by power source circuit 133. Communication circuit 132 receives wireless communication signal 140 and provides sensory information to sensor processing circuit 131. Sensor processing circuit 131 is arranged to communicate to the MCU, where the sensory information may be further processed for application. Example applications include communication to other bionic implants to affect motor functions, muscular contractions, etc. The sensory information is interpreted as touch or feel.

MCU 130 may not be necessary in some implementations. In example application, the patient has damaged a nerve ending in a finger such that touch sensitivity is impaired even though the nerve is still capable of communicating to the brain. In this example, communication circuit 122 corresponds to a signal conditioner that is configured to couple electrical signals (e.g., via one or more electrodes) to the nerve. In another case where the nerve is incapable of communicating to the brain, a different nerve may be used to communicate electrical signals that are associated with sensor 121 to the brain.

Example Process Flow

Figure 2:
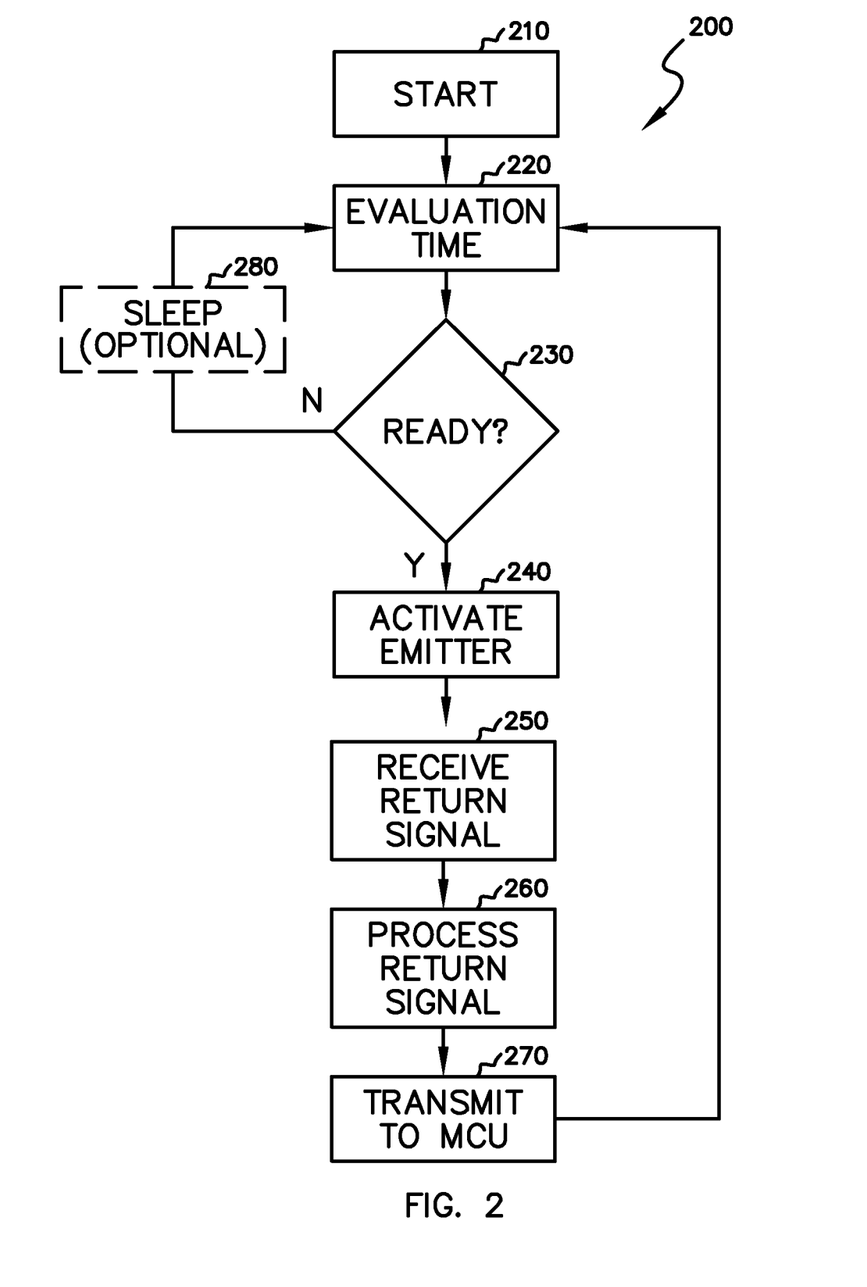
FIG. 2 illustrates an example process flow for another neural prosthetic device.

FIG. 2 illustrates an example process flow 200 for another neural prosthetic device. Process flow 200 may be implemented as software that is stored in a memory device (e.g., a read only memory), as a programmable logic device (PLD), as a digital logic circuit, as operations that are handled by a controller, or any other appropriate mechanism as will become apparent from the present disclosure. Processing begins at block 210 and proceeds to block 220.

At block 220, time is evaluated to determine if an appropriate time has elapsed for activating an emitter. Processing flows from decision block 230 to block 240 when sufficient time has elapsed to begin emitting. Alternatively, processing returns from decision block 230 to block 220 when insufficient time has elapsed to begin emitting a signal. Optional block 280 may be used to place the device in a suspended operating mode (e.g., sleep, conserve power, suspend, etc.) as may be needed.

At block 240, the emitter (or emitters) are activated such that one or more signals are emitted from the neural prosthetic device. Example emitters include: modulated transmitters, ultra-wideband transmitters, wideband transmitters, narrow band transmitters, sweep frequency transmitters, pulse transmitters, RF transmitters, ultrasonic transducers, high frequency LC oscillators and infrared devices. The emitter(s) transmit a signal (or signals) through the tissue that surrounds the implanted device. One or more signals may be reflected from within the tissue, or perhaps from outside of the tissue depending on the environmental conditions that are exerted upon the region of the tissue that surrounds the neural prosthetic device. Continuing to block 250 the return signal is received by the neural prosthetic device (e.g., via a detector circuit, a receiver circuit, a transducer circuit, etc.).

Continuing to block 260, the received signal is processed by a signal processing means to provide an information signal (or signals). Example signal processing means includes: an analog signal processing circuit, a digital signal processing circuit, a Fast Fourier Transform (FFT) circuit, an amplifier circuit, a filter circuit, a correlator circuit, a convolution circuit and an integrator circuit, to name a few. The signal processing means may further include an encoder circuit that is arranged to prepare the information signal for transmission (e.g., provide encryption, coding, compression, etc.).

Flowing to block 270, the information signal (or the coded information signal) is transmitted form the neural prosthetic device to the MCU. Processing returns from block 270 to block 220, where the processing flow cycle repeats again.

Sensory Factors

A single bionic device, or multiple bionic devices, can be implanted in tissue to provide sensory feedback from the various limbs or other parts of the human body that may be inoperable (or impaired) due to nervous system malfunction or damage. The sensory feedback is useful for both functional and safety reasons. Although it is difficult to restore the exact set of neural stimulations that are interpreted in the human body as touch, it is possible to use radio frequency communication techniques to generate sensory data that is similar to human tactile sensation.

Materials can be characterized based on their electrical, magnetic, acoustic and mechanical properties as described by: conductivity, dielectric constant, magnetic permeability, acoustic impedance and sound velocity, to name a few. These materials further vary in their characteristic as a function of frequency, denoting their real and imaginary parts. An antenna can be used as part of a sensor system since the antenna perceives the surrounding environment as a complex impedance. A modulated communication signal, as well as other communication signals can be provided to the antenna. bionic devices can be arranged to provide functions that are analogous to human tactile sensation (e.g., "touch") by emitting (or transmitting) a frequency sensitive signal into a resonant circuit that includes the antenna. Since the surrounding human tissue presents a complex impedance to the load, the tissue exhibits quantifiable characteristics that can be evaluated by the difference between the desired operating frequency of the resonant circuit and the actual resonant frequency.

The complex impedance of the antenna/resonant circuit can be indexed according to a number of test frequencies. The vectors can then be evaluated with a signal processor such as a vector analyzer, an inverse FFT algorithm, or some other processing that provides a time domain representation of the antennas performance. Wider frequency ranges of operation can be used to permit collection of more information. In some instances, a very wide band (UWB) signal may be desirable since the wide band signal contains a significant amount of information related to the environment surrounding the sensor.

In one example, a modulated signal in one portion of the RF spectrum is transmitted into the human tissue (e.g. TDMA modulated UHF) surrounding the sensor device. The modulated signal may be the same communication signal that is used for normal BION microstimulator communication, or it could be a separate signal. RF communication signals are affected in number of complex ways when transmitted into tissue such as in the body of a patient. At the skin boundary, some RF signals are transmitted out of the tissue while others are reflected back towards the tissue. The reflectivity of the tissue at the boundary is dependent on the complex impedances of the tissue(s) and of the external environment. For example, the complex RF impedance of the surrounding tissue changes when the shape of the tissue immediately surrounding the bionic implant device changes due to external pressure. The complex impedance is also affected by the boundary region when the tissue is adjacent a medium different from air (e.g., water causes a change in the impedance at the surface). By sensing the changes in impedance at the surface, as well as changes in the impedance surrounding the bionic implant, a model can be constructed for sensing human touch.

One very convenient way to achieve sensing human touch is to create a complex correlation between the desired transmitted signal and the actual transmitted signal, as affected by the environment. In one example, an analog multiplier-type circuit is employed to multiply the complex modulated signal proved to a final amplifier stage by either the signal at the output of the final amplifier or the signal at the output of a matching network. The output of the multiplier can be integrated and digitized for transmission over a regular interval (e.g., 100 times per second). A receiver circuit can receive the transmissions and communicate the information to the brain (e.g., through an implanted bionic receiver device).

In another example, a complex digital multiplier circuit is employed consisting of XOR gates or the like, followed by an integrator. Since the modulated signal is used as a reference, the modulation itself is absent from the resulting signal. For more sophisticated systems, a half analog and half digital circuit can be utilized. A maximum amount of information can be recovered with information such as time and modulation, since in this way reflections can be sensed.

In general terms, a reference complex impedance can be generated and then variations from this reference complex impedance can be evaluated to identify changes in the environment about the implanted sensor device. Very small changes in the phase and/or amplitude of the signals can be identified with this method. Also changes in the frequency may also be evaluated with this method.

While pressure information can be inferred from impedance due to tissue deformation, other effects, such as changes in external conductivity and dielectric properties can also be measured. Therefore, the proposed sensor devices can detect close objects without contact and can further be arranged to differentiate between substances such as wood, metal, plastic and water, to name a few. This sensory data can be combined with other information to formulate a highly informative artificial sensor (e.g., infrared sensing can be combined with impedance sensing, etc.)

The presentation of sensory information to the brain can be accomplished through direct connection to the remaining peripheral (or central) nervous system or converted to audio or visual signals. The brain's natural ability to uniquely interpret recurring stimuli can generate a sensory map to the provided sensory data.

Example Neural Prosthetic Devices

FIGS. 3-7 are block diagrams for various example neural prosthetic devices.

Figure 3:
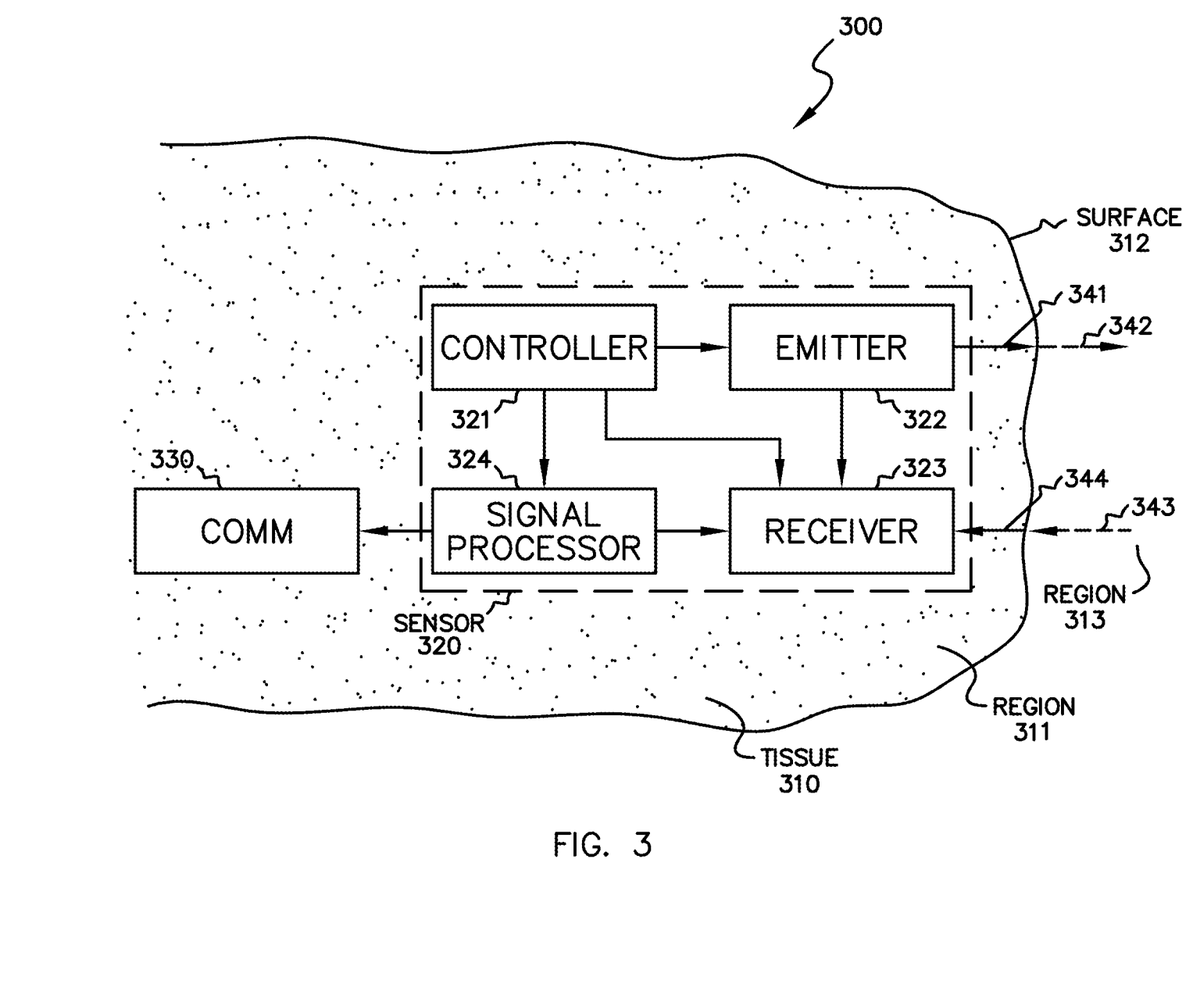
FIG. 3 is a block diagram for yet another example neural prosthetic device.

FIG. 3 is a block diagram illustrating an example neural prosthetic device 300 that includes sensor circuit 320 and communication circuit 330. Sensor circuit 320 includes controller 321, emitter 322, receiver 323 and signal processor 324. Controller 321 is arranged to coordinate the various timing and control signals that are necessary to provide for proper operation of emitter 322, receiver 323 and signal processor 324. An output of the signal processor 324 is coupled to the communication circuit 330 for communication of sensory information to the brain as previously described.

The sensor 320 is implanted in the tissue 310 of a person in a region 311 near a surface 312 where sensory data is relevant (e.g., the tip of a finger). Emitter 322 is configured to provide an emitted signal 341 when selectively activated by controller 321. As illustrated, emitted signal 341 is transmitted towards surface 312 through region 311. A portion of emitted signal 341 may be reflected back from surface 312 into tissue region 311. Another portion of emitted signal 341 may be transmitted into adjacent region 313 as illustrated by signal 342. Adjacent region 313 is external to tissue region 310 and may contain foreign matter such as an object that the person is in contact with and/or a number of other environmental conditions such as: heat, cold, water, light, etc. The various conditions and forces exerted on signal 342 may result in another reflected signal 343.

Receiver 323 is configured to receive return signal 344 when selectively activated by controller 321. Return signal 344 consists of all reflected signals that result from emitted signal 341. Signal processor 324 is configured to condition the received return signal and provide the resulting signal to communication circuit 330 for communication of sensory information. Signal processor 324 may be arranged to provide a number of signal processing functions including, but not limited to: analog signal processing, digital signal processing, FFTs, amplification, attenuation, filtering, correlation, convolution, integration, time displacement, spectrum analysis, return signal strength, peak signal strength, average signal strength, mean signal strength and return signal phase, to name a few. The signal processing means may further include an encoder circuit that is arranged to prepare the information signal(s) for transmission (e.g., provide encryption, coding, compression, etc.).

Figure 4:
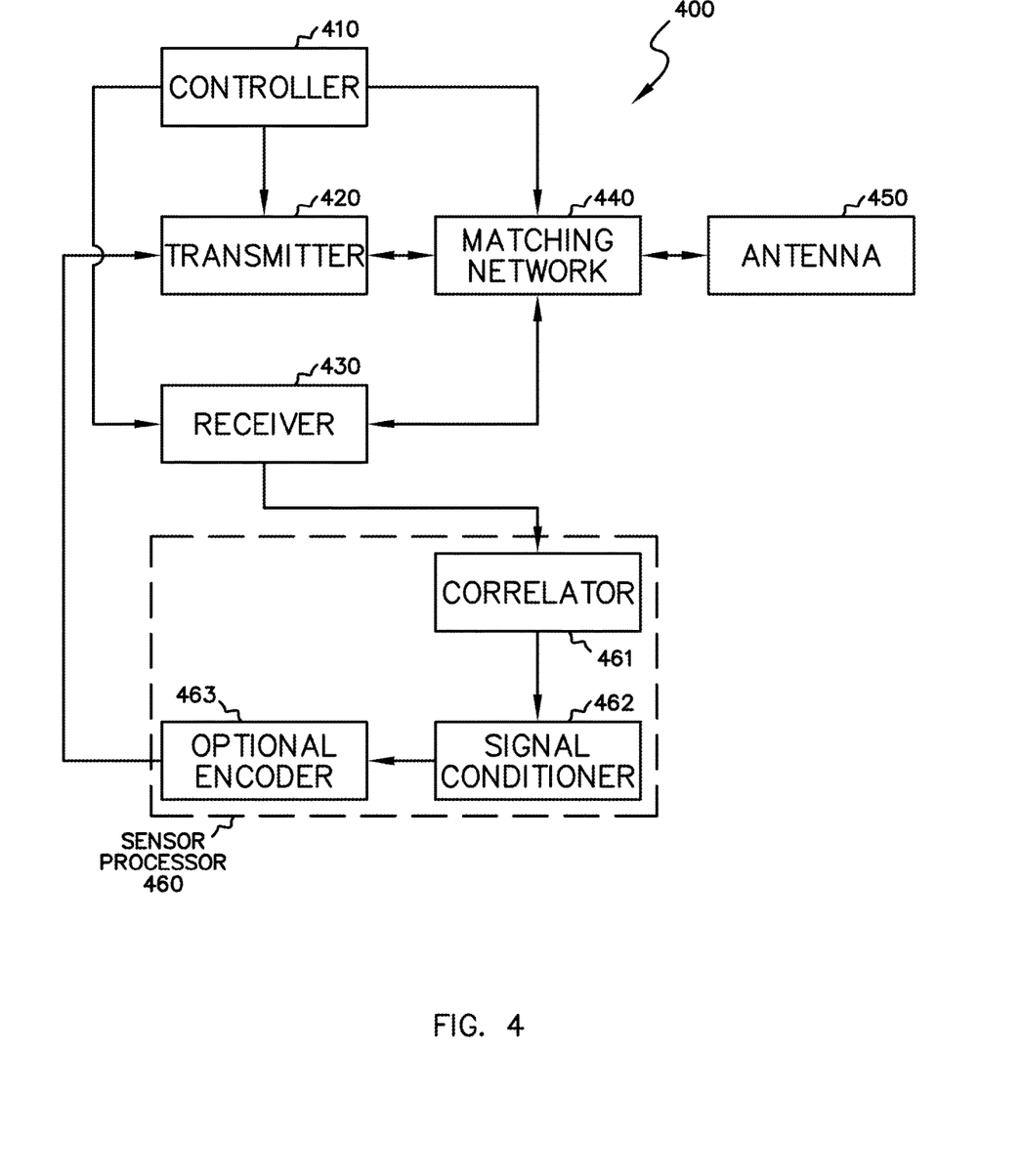
FIG. 4 is a block diagram for still another example neural prosthetic device.

FIG. 4 is a block diagram for still another example neural prosthetic device 400. The example neural prosthetic device 400 includes: controller 410, transmitter 420, receiver 430, matching network 440, antenna 450 and sensor processor 460.

Controller 410 is arranged in cooperation with transmitter 420, receiver 430 and matching network 440. Transmitter 420 and receiver 430 are selectively coupled to antenna 450 via matching network 440. For this example device, transmitter 420 is configured to operate similar to emitter 322 described previously with respect to FIG. 3. Also, receiver 430 is arranged to operate similar to receiver 323 from FIG. 3. Since transmitter 420 and receiver 430 share the use of a single antenna, controller 410 must be arranged to ensure that the operation of receiver 430 and transmitter 420 do not interfere with one another.

Sensor processor 460 includes correlator 461, signal conditioner 462 and an optional encoder 463. Correlator 461 includes an input that is coupled to an output of receiver 430 and an output that is coupled to signal conditioner 462. Signal conditioner 462 includes an output that is coupled to an input of optional encoder 463. Signal conditioner 462 is configured to provide any desired function such as gain, attenuation, filtering, limiting, as well as other signal processing functions as described previously. The optional encoder is arranged to encode signals from the signal conditioner for communication to the MCU via transmitter 420.

Sensor Processor 460 is arranged to receive an output signal from receiver 430 and provide an input signal to transmitter 420. Controller 410 is arranged to selectively operate transmitter 420 and matching network 440 for communication to an MCU unit without the use of any additional circuitry. In other words, antenna 450 and matching network 440 can be tuned for two operations. The first operation corresponds to transmission of a signal through tissue for sensory purposes. The second operation corresponds to transmission of a communication signal to the MCU.

Figure 5:
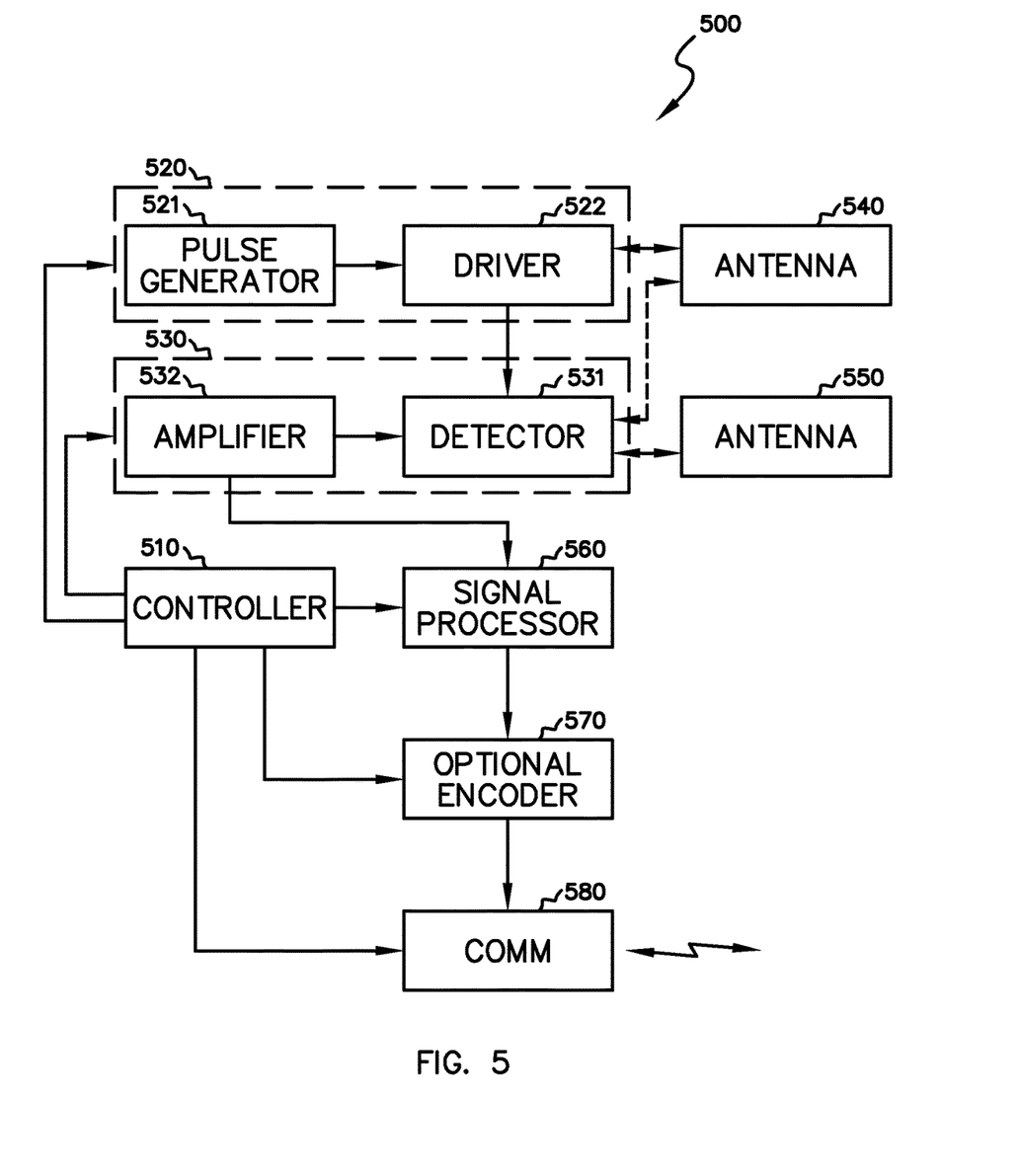
FIG. 5 is a block diagram for yet still another example neural prosthetic device.

FIG. 5 is a block diagram for yet still another example neural prosthetic device 500. Device 500 includes controller 510, transmitter 520, receiver 530, one or more antenna circuits 540, 550, signal processor 560, an optional encoder 570 and communication system 580.

Controller 510 is arranged in communication with at least one of transmitter 520, receiver 530, signal processor 560, optional encoder 570 and communication system 580. Transmitter 520 includes a pulse generator 521 that is arranged to selectively couple pulse signals to driver 522. Driver 522 is arranged to transmit a pulse signal via antenna circuit 540. Receiver 530 includes detector 531 that is coupled to amplifier 532, where reflected signals that are received by antenna circuit 550 are detected and amplified. The amplified signal is provided to signal processor 560, which is arranged to provide gain, attenuation, filtering, as well as any other desired signal processing function. The output of signal processor 560 can be encoded by encoder 570 for communication via communication system 580.

Antenna circuit 550 can be eliminated when antenna 540 is shared between transmitter 520 and receiver 530. In one example, the pulse generator is arranged to provide an ultra-wideband signal pulse via antenna 540. For this example, the receiver is arranged to capture the reflected signal and extract various signal characteristics with signal processor 560. Example characteristics of the reflected signal include: return signal spectrum, signal amplitudes for the return signal spectrum, peak return signal frequency, return signal phase, signal dispersion and other useful characteristics. These various characteristics may be used to identify different materials that are proximate to the sensor, different pressures that are exerted about the tissue surrounding the sensor, as well as any other appropriate condition.

As described previously, wider frequency ranges of operation can be used to permit collection of a significant amount of information related to the environment surrounding the sensor. For this example, the pulse generator can be arranged to provide ultra-short pulses such that the received signals can be time domain separated from the transmitted signal, similar to a conventional radar system. To accomplish this, the round-trip time between the transmission of the pulse and the reception of a reflected pulse is on the order of 200 ps for a 1 cm distance. In some applications, pulses on the order of 50 ps may be necessary to generate sensory data to detect skin deformation.

Figure 6:
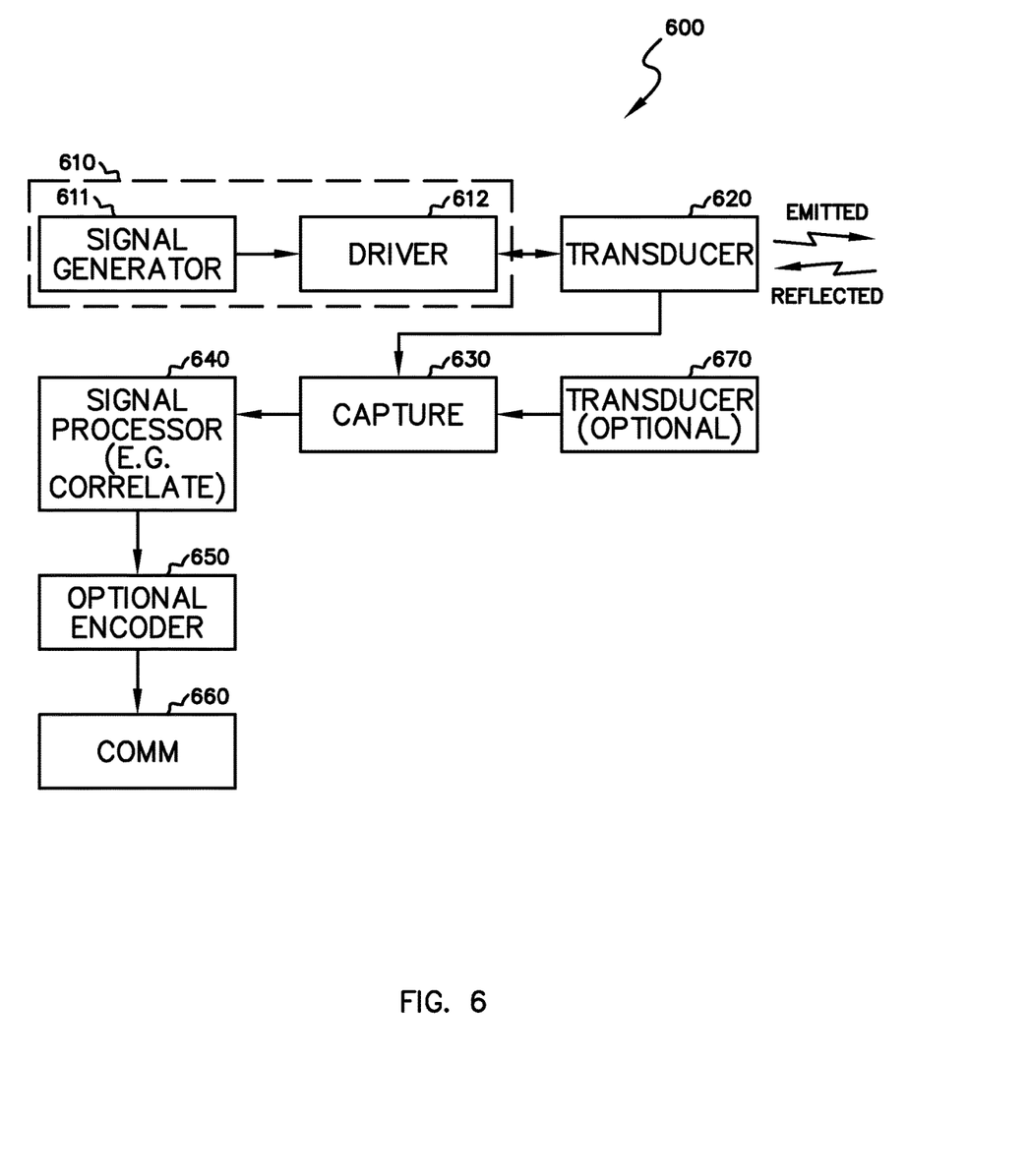
FIG. 6 is a block diagram for still yet another example neural prosthetic device.

FIG. 6 is a block diagram for still yet another example neural prosthetic device 600. Device 600 includes transmitter 610, transducer 620, capture block 630, signal processor 640, optional encoder 650, optional communication system 660 and optional transducer 670.

Transmitter 610 includes signal generator 611 that is arranged in communication with driver 612 to provide a suitable input signal for transducer 620 to transmit an emitted signal. A reflected signal is received from either transducer 620 or optional transducer 670 and stored in capture block 630. Signal processor 640 is arranged to provide various signal processing functions to the stored signals resulting from the reflected signals. Optional encoder 650 and communication system 660 operate similar to that previously described.

In one example, signal generator 611 is arranged to provide a pulsed signal. In another example, signal generator 611 is arranged to provide a chirped signal. In still another example, signal generator 611 is arranged to provide a pseudo-noise like modulation signal. In yet another example, transducer 620 is capable of providing an ultrasonic signal as the emitted signal. In still yet another example, transducer 620 is arranged to provide sense pressure changes in the surrounding tissue. In yet another implementation, transducer 620 is capable of transmitting/sensing an audio signal or a subsonic signal. The basic function of the transducer is that of a signal emitter and receiver for any of a number of sensing applications.

An ultrasonic sensor application may be implemented with the topology illustrated in FIG. 6. Ultrasound travels through tissue at a rate on the order of 1200-1700 meters/second. For frequencies on the order of 10 MHz, the wavelength is on the order of 0.1 mm, which provides adequate resolution for sensory data. Such an ultrasonic transducer can be used to measure skin deformations in a different manner than the RF communication signals.

Figure 7:
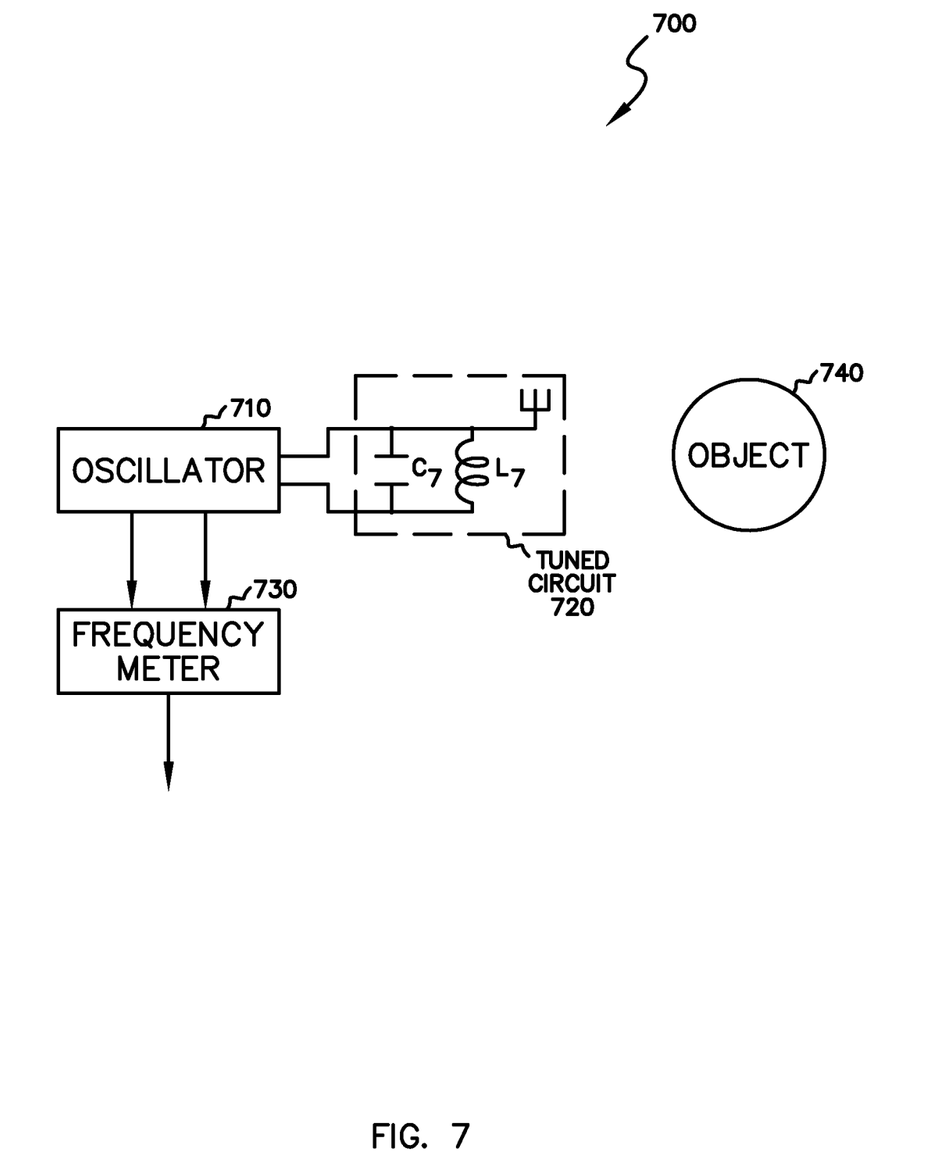
FIG. 7 is a block diagram for a neural prosthetic device that is arranged sense changes in impedance of an antenna by sensing frequency changes.

FIG. 7 is a block diagram for neural prosthetic device 700 that is arranged to sense changes in impedance of an antenna by sensing frequency changes. The device 700 includes an oscillator 710, tuned circuit 720 and frequency meter 730.

The oscillator 710 is arranged to excite the tuned circuit 720, which includes capacitor C7, inductor L7 and an antenna. Frequency meter 730 is arranged to evaluate resonant frequencies associated with tuned circuit 720. Frequency meter 730 provides one or more output signals, which can subsequently be coded and communicated to an MCU as previously described.

The illustrated example is arranged to provide one particular type of sense (e.g., touch) by detecting a change in the impedance of an antenna. As the antenna is brought into close proximity with an object (e.g., 740), the impedance of the antenna changes based on electrical effects. Inductor L7 and capacitor C7 form a resonance with the antenna. The resonant frequency of tuned circuit 720 is thus varied based on a distance between object 740 and the antenna.

The object may be any type of material such as metal, stone, wood, water, etc. Each object has its own particular effect on the inductive and/or capacitive characteristics of the tuned circuit. When the object and the implantable device are proximal to each other, the total amount of the LC coupled to the oscillator is affected. For example, if the object proximal to the LC circuit is a material that affects the capacitive component of the LC circuit, then the total amount of the inductance and capacitance coupled to the power oscillator is the sum of L7 and C7 plus the capacitance associated with the object. The change in the total amount of the inductance and capacitance causes a corresponding change in the impedance of the LC resonant circuit and consequently changes the frequency of the oscillator. By measuring the corresponding change in the frequency and comparing the same with a table of values associated with different materials, the characteristic of the material namely, metal, wood, or any other type of material can be identified.

It is further contemplated that in the event pressure is exerted on the tissue proximal to the implantable device, the change in the physical characteristics of the compressed tissue accordingly produces a change in the total inductance and capacitance of the LC circuit. As described above, the change in the value of the LC circuit results in a corresponding change in the frequency of the oscillator. In this manner, the implantable device is capable of measuring pressure proximal thereto.

Figure 8:
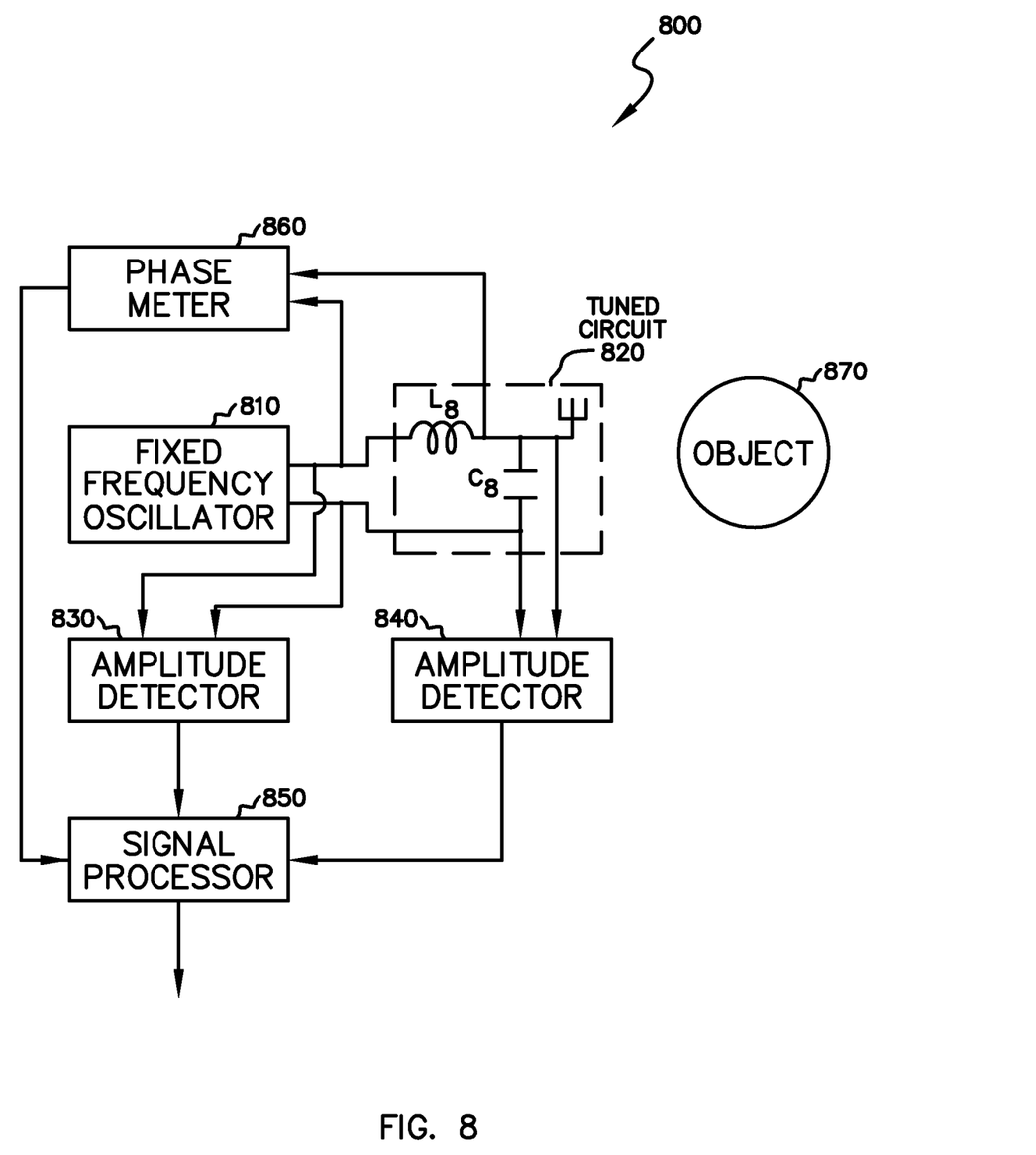
FIG. 8 is a block diagram for a neural prosthetic device that is arranged sense changes in impedance of an antenna by sensing amplitude and phase changes.

FIG. 8 is a block diagram for neural prosthetic device 800 that is arranged to sense changes in impedance of an antenna by sensing amplitude and phase changes. Device 800 includes fixed frequency oscillator 810, tuned circuit 820, amplitude detectors 830, 840, signal processor 850 and phase meter 860.

Fixed frequency oscillator 810 is coupled to tuned circuit 820, which includes inductor L8 and capacitor C8 that are coupled to an antenna. Phase meter 860 is coupled across inductor L8. Amplitude detector 830 is coupled to an input side of tuned circuit 820, while amplitude detector 840 is coupled to an output side of tuned circuit 820. Signal processor 850 is arranged to receive various inputs such as the output of amplitude detectors 830, 840 and the output of phase meter 860. The impedance of tuned circuit 820 is varied based on the proximity of the antenna to an object 870.

In one example, fixed frequency oscillator 810 is a crystal oscillator for generating signals that are supplied to the inductor L8 and the capacitor C8 of the tuned circuit 820. The first amplitude detector 830 is arranged to measure the amplitude of the signals generated by oscillator 810, while the second amplitude detector 840 is arranged to measure the amplitude of the signal across capacitor C8. The two amplitudes are evaluated by signal processor 850, which can determine a ratio of the respective amplitudes.

The physical and electrical properties of the object affect the inductance and capacitance of tuned circuit 820. A change in the phase shift and also a change in the ratio of the amplitudes of the respective generated signals is observed as a result in the changed impedance of tuned circuit 820. Signal processor 850 is arranged to evaluate the various sensory inputs and identify touch-like characteristics as amplitude change and phase change.

Figure 9:
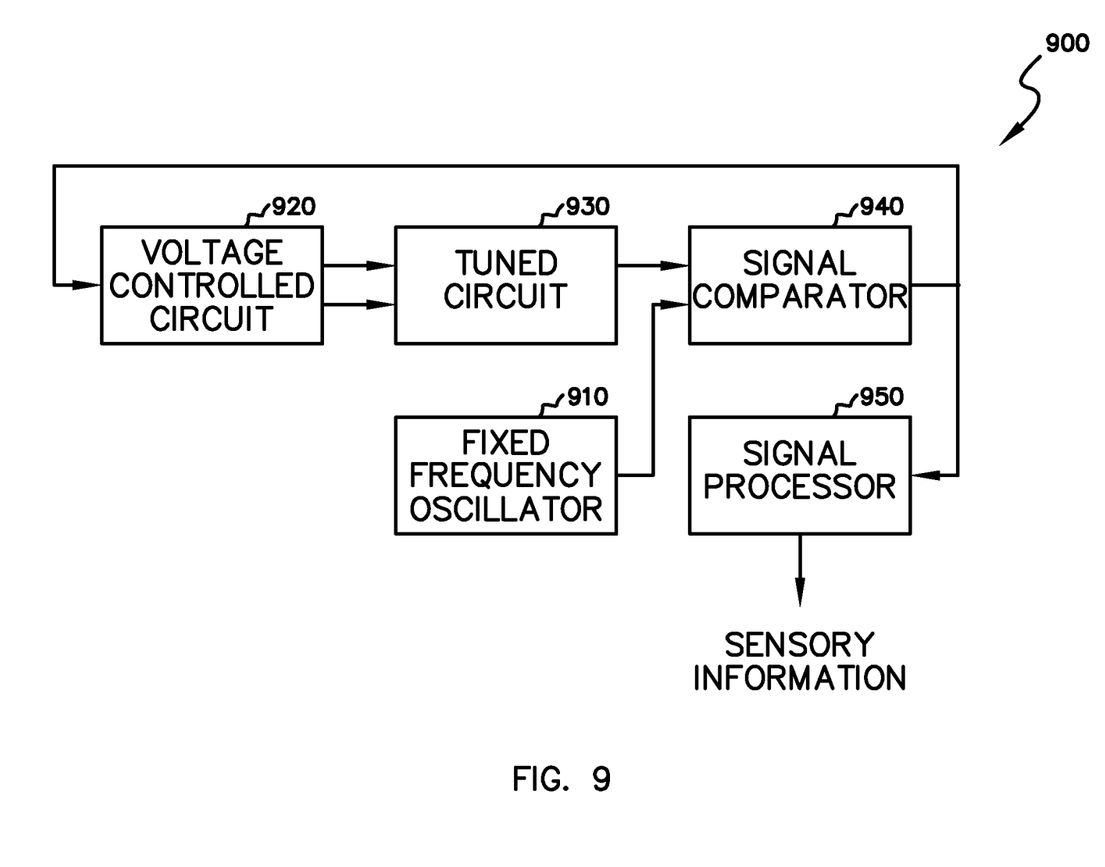
FIG. 9 is a block diagram for a neural prosthetic device that is arranged sense changes in impedance of an antenna by locking a reference signal to a variable signal, arranged in accordance with at least one aspect of present invention.

FIG. 9 is a block diagram for neural prosthetic device 900 that is arranged to sense changes in the impedance of an antenna by locking a reference signal to a variable signal, using a closed loop control topology (e.g., frequency locked loop, phase locked loop, delay locked loop, etc.). Device 900 includes fixed frequency oscillator 910, voltage controlled circuit 920, tuned circuit 930, signal comparator 940 and signal processor 950.

Fixed frequency oscillator 910 is arranged to provide a reference signal. Voltage controlled circuit 920 and tuned circuit 930 are arranged to operate together as a voltage controlled oscillator to provide a variable signal. Although voltage controlled circuit 920 is responsive to a control signal (Vcontrol), tuned circuit 930 has a variable resonant frequency that is responsive to the environmental conditions. The result is that the variable signal is affected by the environmental conditions that are surrounding the tissue near the device. The signal comparator 940 is arranged to compare the variable signal to the reference signal to provide closed loop feedback in the form of the control signal (Vcontrol). Signal processor 950 can be employed to evaluate the control signal and identify the relevant sensory information.

Signal comparator 940 can be arranged to compare frequency, phase and amplitude of the signals to adjust the control signal. A phase locked loop topology can be used to lock the variable frequency to the reference frequency. The resulting control voltage indicates the sensory information since the tuned circuit will have a different resonant condition in each different environment.

Although the electronic systems and circuits are illustrated by various individual blocks, the electronic system should not be interpreted as limited to these discrete blocks. One or more of the electronic system blocks may be combined or separated into one or more blocks that provide a similar functionality. The invention is not limited to the embodiments described above, but rather covers all modifications, alternatives and equivalents that fall within the spirit and scope of the invention. Since many embodiments of the invention can be made without departing from the spirit and scope of the invention, the invention resides in the claims hereinafter appended.

What is claimed is:

1. An implantable neural prosthetic sensor device that is configured to be implanted in tissue, comprising:
    a tuned circuit that has a resonant frequency that varies as influenced by an environmental condition associated with the tissue, wherein the tuned circuit comprises a radio frequency (RF) sensor, the RF sensor being configured to perceive the tissue as a complex impedance, the resonant frequency of the tuned circuit being responsive to the complex impedance perceived by the RF sensor, and wherein the complex impedance perceived by the RF sensor is responsive to the environmental condition associated with the tissue; and
    a signal processor that is configured to evaluate the complex impedance perceived by the RF sensor to provide thereby sensory information for a neural prosthetic based on the tuned circuit resonant frequency.

2. The implantable neural prosthetic sensor device of claim 1, wherein the environmental condition comprises at least one of: ambient temperature of the tissue, surface temperature of a surface of the tissue, pressure exerted on the surface by a foreign object, heat exerted on the surface by the foreign object, cold exerted on the surface by the foreign object, and deformation of a region of tissue about the prosthetic sensor device.

3. The implantable neural prosthetic sensor device of claim 1, further comprising:
    a fixed frequency oscillator that is arranged to generate a first signal having a first frequency;
    a voltage controlled oscillator comprising a voltage controlled circuit and the tuned circuit, said voltage controlled circuit coupled to the tuned circuit, said voltage controlled oscillator being responsive to a control signal, wherein the voltage controlled oscillator is arranged to generate a second signal having a second frequency in response to the control signal, wherein the second frequency of the voltage controlled oscillator varies in response to environmental conditions associated with the tissue; and
    a signal comparator arranged to compare the first frequency to the second frequency to provide thereby the control signal such that the second frequency is substantially matched to the first frequency.

4. An implantable neural prosthetic sensor device that is configured to be implanted in tissue, comprising:
    a fixed frequency oscillator that is arranged to generate a first signal having a first frequency;
    a variable frequency oscillator that includes a tuned circuit, said variable frequency oscillator being responsive to a closed loop control signal, wherein the variable frequency oscillator is arranged to generate a second signal having a second frequency, wherein the resonant frequency of the tuned circuit is responsive to environmental conditions associated with the tissue, the tuned circuit comprises a radio frequency (RF) sensor, the RF sensor being configured to perceive the tissue as a complex impedance, the resonant frequency of the tuned circuit being responsive to the complex impedance perceived by the RF sensor, and wherein the complex impedance perceived by the RF sensor is responsive to the environmental conditions associated with the tissue;
    a signal comparator that is arranged to compare the first frequency to the second frequency to provide thereby the closed loop control signal; and
    a signal processor configured to evaluate the complex impedance perceived by the RF sensor to provide thereby sensory information for a neural prosthetic associated with the environmental conditions associated with the tissue based on the closed loop control signal.

5. The implantable neural prosthetic sensor device of claim 4, wherein the tuned circuit comprises an inductor-capacitor (LC) tank circuit, wherein at least one of a capacitance and an inductance associated with the LC tank circuit is altered in response to the environmental conditions associated with the tissue.

6. An implantable neural prosthetic sensor device that is configured to be implanted into tissue, comprising:
    a fixed frequency oscillator that is arranged to generate a first signal having a first frequency, a first amplitude, and a first phase;
    a tuned circuit that is coupled to the fixed frequency oscillator and arranged to receive the first signal, wherein the tuned circuit is arranged to provide a second signal having a second frequency, a second amplitude, and a second phase, wherein at least one of the second frequency, the second amplitude, and the second phase is altered as influenced by the tissue environment; and a signal processor circuit that is arranged to compare the first signal to the second signal to provide sensory information that is associated with the environmental conditions associated with the tissue, wherein the tuned circuit comprises a radio frequency (RF) sensor, the RF sensor being configured to perceive the tissue as a complex impedance;

wherein at least one of the second frequency, the second amplitude, and the second phase is responsive to the complex impedance perceived by the RF sensor;

wherein the complex impedance perceived by the RF sensor is responsive to the tissue environment; and wherein the signal processor circuit is configured to evaluate the complex impedance perceived by the RF sensor to provide sensory information for a neural prosthetic based on the complex impedance perceived by the RF sensor.

7. The implantable neural prosthetic sensor device of claim 6, wherein the signal processor circuit comprises at least one of: an amplitude detector, a phase detector, a frequency detector, an amplitude comparator, a phase comparator, and a frequency comparator.

8. The implantable neural prosthetic sensor device of claim 6, further comprising at least one of: a communication circuit that is arranged to communicate the sensory information to a master control unit, a capture circuit that is arranged to store the sensory information, and an encoder that is arranged to encode the sensory information in a data signal.

9. The implantable neural prosthetic sensor device of claim 1 wherein the tuned circuit comprises an inductor, a capacitor, and the RF sensor.

10. The implantable neural prosthetic sensor device of claim 1 wherein:
the RF sensor is an antenna;
the antenna perceives the tissue as the complex impedance;
the resonant frequency of the tuned circuit is responsive to the complex impedance perceived by the antenna; and
the complex impedance perceived by the antenna is responsive to the environmental conditions associated with the tissue.

11. The implantable neural prosthetic sensor device of claim 4 wherein the signal comparator provides the closed loop control signal such that the second frequency matches the first frequency.

12. The implantable neural prosthetic sensor device of claim 4 wherein the tuned circuit comprises an inductor, a capacitor, and the RF sensor.

13. The implantable neural prosthetic sensor device of claim 4 wherein:
the RF sensor is an antenna;
the antenna perceives the tissue as the complex impedance;
the resonant frequency of the tuned circuit is responsive to the complex impedance perceived by the antenna; and
the complex impedance perceived by the antenna is responsive to the environmental conditions associated with the tissue.

14. The implantable neural prosthetic sensor device of claim 6 wherein the tissue environment is the presence of an object in proximity to the tissue.

15. The implantable neural prosthetic sensor device of claim 14 wherein the sensory information is a property of the object.

16. The implantable neural prosthetic sensor device of claim 14 wherein the sensory information is the presence of a particular material in the object.

17. The implantable neural prosthetic sensor device of claim 6 wherein the tuned circuit comprises an inductor, a capacitor, and RF sensor.

18. The implantable neural prosthetic sensor device of claim 6 wherein:
the RF sensor is an antenna;
the antenna perceives the tissue as the complex impedance;
at least one of the second frequency, the second amplitude, and the second phase is responsive to the complex impedance perceived by the antenna; and
the complex impedance perceived by the antenna is responsive to the tissue environment.

* * * * *